United States Patent [19]
Ohrbom et al.

[11] Patent Number: 6,084,038
[45] Date of Patent: *Jul. 4, 2000

[54] CURABLE COATING COMPOSITIONS CONTAINING BLENDS OF CARBAMATE-FUNCTIONAL COMPOUNDS

[75] Inventors: Walter H Ohrbom, Hartland Township; Gregory G. Menovcik, Farmington Hills; Donald L. St. Aubin, Commerce Township; John E. Boisseau, Bloomfield Hills; John W. Rehfuss, West Bloomfield; John D. McGee; Brian D. Bammel, both of Highland, all of Mich.; Danielle Regulski, Charleston, S.C.; Christopher Bradford, Ann Arbor, Mich.

[73] Assignee: BASF Corporation, Southfield, Mich.

[ * ] Notice: This patent is subject to a terminal disclaimer.

[21] Appl. No.: 09/184,195

[22] Filed: Nov. 2, 1998

Related U.S. Application Data

[63] Continuation-in-part of application No. 08/997,317, Dec. 23, 1997, Pat. No. 5,994,479, which is a continuation-in-part of application No. 08/886,321, Jul. 1, 1997, Pat. No. 5,872,195, which is a continuation of application No. 08/698,529, Aug. 15, 1996, Pat. No. 5,854,385, which is a continuation of application No. 08/540,274, Oct. 6, 1995, abandoned, and application No. 08/333,917, Nov. 3, 1994, Pat. No. 5,744,550, and application No. 08/176,608, Jan. 3, 1994, abandoned, and application No. 08/287,351, Aug. 8, 1994, abandoned, which is a continuation-in-part of application No. 08/098,177, Jul. 28, 1993, abandoned, and application No. 08/867,547, Jun. 2, 1997, which is a continuation of application No. 08/513,587, Aug. 10, 1995, Pat. No. 5,726,244, and application No. 08/547,513, Oct. 24, 1995, Pat. No. 5,726,274, which is a division of application No. 08/361,344, Dec. 21, 1994, abandoned, and a division of application No. 08/547,174, Oct. 24, 1995, Pat. No. 5,723,552, which is a division of application No. 08/361,344, and a division of application No. 08/698,524, Aug. 15, 1996, Pat. No. 5,792,810, which is a continuation of application No. 08/550,880, Oct. 6, 1995, abandoned, and application No. 08/698,526, Aug. 15, 1996, Pat. No. 5,760,127, which is a continuation of application No. 08/686,929, Oct. 6, 1995, and application No. 08/667,261, Jun. 20, 1996, Pat. No. 5,777,048, and application No. 08/698,528, Aug. 15, 1996, Pat. No. 5,756,213, which is a continuation of application No. 08/540,275, Oct. 6, 1995, abandoned, and application No. 08/698,522, Aug. 15, 1996, Pat. No. 5,827,930, which is a continuation of application No. 08/540,277, Oct. 6, 1995, abandoned, and application No. 08/698,523, Aug. 15, 1996, Pat. No. 5,770,650, which is a continuation of application No. 08/540,279, Oct. 6, 1995, abandoned, and application No. 08/886,321, and application No. 08/831,810, Apr. 2, 1997, and application No. 08/333,804, Nov. 3, 1994

[60] Provisional application No. 60/021,068, Jul. 1, 1996.

[51] Int. Cl.[7] .............................. C08G 8/28; C08G 59/14; C08L 63/00; C08L 67/04
[52] U.S. Cl. ......................... 525/481; 525/488; 525/510; 525/514; 525/528; 525/129; 525/144; 525/146; 525/163; 525/423.1
[58] Field of Search .................................... 525/481, 488, 525/510, 514, 528, 129, 144, 146, 163, 423.1

[56] References Cited

U.S. PATENT DOCUMENTS 5,872,195  2/1999  Green et al. ............................. 525/481

*Primary Examiner*—Duc Truong
*Attorney, Agent, or Firm*—Anna M. Budde

[57] ABSTRACT

The present invention provides a curable coating composition that includes at least three components. The coating composition includes a component (a) having at least one carbamate group or urea group and having a lactone or hydroxy carboxylic acid moiety. The second component (b) of the coating composition is one or more of three materials. First, the second component can be a polymer resin (b)(1) comprising active hydrogen-containing functional groups reactive with the third component(c). Secondly, the second component can be a compound (b)(2) having at least one carbamate group or terminal urea group according to the invention and having at least two linking groups that are urethane or urea. Finally, the second component can be a compound (b)(3) having at least two groups selected from carbamate groups, terminal urea groups, or combinations of the two and at least four urethane or urea linking groups. The third component of the coating composition is a curing agent that is reactive with the first two components. Preparation of coated articles using the compositions of the invention is also disclosed.

54 Claims, No Drawings

CURABLE COATING COMPOSITIONS CONTAINING BLENDS OF CARBAMATE-FUNCTIONAL COMPOUNDS

The present application is a continuation-in-part of Green et al, U.S. application Ser. No. 08/997,317, filed Dec. 23,1997 now U.S. Pat. No. 5,994,479, which is continuation-in-part of each of the following: Green et al., U.S. application Ser. No. 08/886,321, filed Jul. 1, 1997 now U.S. Pat. No. 5,872,195, which is a continuation of provisional application Ser. No. 60/021,068, filed Jul. 1, 1996; McGee et al., U.S. application Ser. No. 08/698,529, filed Aug. 15, 1996 now U.S. Pat. No. 5,854,385, which is a continuation of Ser. No. 08/540,274, filed Oct. 6, 1995, now abandoned; Menovcik et al., U.S. application Ser. No. 08/333,917, filed Nov. 3, 1994, now U.S. Pat. No. 5,744,550, issued Apr. 28, 1998; U.S. application Ser. No. 08/176,608, filed Jan. 3, 1994, now abandoned; Rehfuss et al., U.S. application Ser. No. 08/287,351, filed Aug. 8, 1994 now abandoned, which is a continuation-in-part of Ser. No. 08/098,177, filed Jul. 28, 1993, now abandoned; McGee et al., U.S. application Ser. No. 08/867,547, filed Jun. 2, 1997 now allowed, which is a continuation of U.S. application Ser. No. 08/513,587, filed Aug. 10, 1995, now U.S. Pat. No. 5,726,244, issued Mar. 10, 1998; Menovcik et al., U.S. application Ser. No. 08/547,513, filed Oct. 24, 1995, now U.S. Pat. No. 5,726,274, issued Mar. 10, 1998, which is a division of U.S. application Ser. No. 08/361,344, filed Dec. 21, 1994, now abandoned; Menovcik et al., U.S. application Ser. No. 08/547,174, filed Oct. 24, 1995, now U.S. Pat. No. 5,723,552, issued Mar. 3, 1998, which is a divisional of U.S. application Ser. No. 08/361,344, filed Dec. 21, 1994, now abandoned; Menovcik et al., U.S. application Ser. No. 08/698,524, filed Aug. 15, 1996, now U.S. Pat. No. 5,792,810, issued Aug. 11, 1998, which is a continuation of Ser. No. 08/550,880, filed Oct. 6, 1995 now abandoned; Bammel et al., U.S. application Ser. No. 08/698,526, filed Aug. 15, 1996, now U.S. Pat. No. 5,760,127, issued Jun. 2, 1998, which is a continuation of U.S. application Ser. No. 08/686,929, filed Oct. 6, 1995 ; Ohrbom et al., U.S. application Ser. No. 08/667,261, filed Jun. 20, 1996, now U.S. Pat. No. 5,777,048, issued Jul. 7, 1998; Ohrbom et al., U.S. application Ser. No.08/698,528, filed Aug. 15, 1996, now U.S. Pat. No. 5,756,213, issued May 26, 1998, which is a continuation of U.S. application Ser. No. 08/540,275, filed Oct. 6, 1995, now abandoned; Ohrbom et al., U.S. application Ser. No. 08/698,522, filed Aug. 15, 1996 now U.S. Pat. No. 5,827,930, which is a continuation of U.S. application Ser. No. 08/540,277, filed Oct. 6, 1995, now abandoned; McGee et al., U.S. application Ser. No. 08/698,523, filed Aug. 15, 1996, now U.S. Pat. No. 5,770,650, issued Jun. 23, 1998, which is a continuation of U.S. application Ser. No. 08/540,279, filed Oct. 6, 1995, now abandoned; Green et al., U.S. application Ser. No. 08/886,321, filed Jul. 1, 1997, now U.S. Pat. No. 5,872,195, which is a continuation of provisional application Ser. No. 60/021,068, filed Jul. 1, 1996; Bammel et al., U.S. application Ser. No. 08/831,810, filed Apr. 2, 1997, now pending; Ohrbom et al, U.S. application Ser. No. 08/333,804, filed Nov. 3, 1994 now pending.

FIELD OF THE INVENTION

This invention concerns curable coating compositions, especially compositions for high-gloss topcoats, particularly for clearcoats of color-plus-clear composite coatings.

BACKGROUND OF THE INVENTION

Curable, or thermosettable, coating compositions are widely used in the coatings art, particularly for topcoats in the automotive and industrial coatings industry. Color-plus-clear composite coatings are particularly useful as topcoats for which exceptional gloss, depth of color, distinctness of image, or special metallic effects are desired. The automotive industry has made extensive use of these coatings for automotive body panels.

Single-layer topcoats and the clearcoats of color-plus-clear composite coatings, however, require an extremely high degree of clarity and gloss to achieve the desired visual effect. Such coatings also require a low degree of visual aberrations at the surface of the coating in order to achieve the desired visual effect such as high distinctness of image (DOI). As such, these coatings are especially susceptible to a phenomenon known as environmental etch. Environmental etch manifests itself as spots or marks on or in the finish of the coating that often cannot be rubbed out. It is often difficult to predict the degree of resistance to environmental etch that a high gloss topcoat or color-plus-clear composite coating will exhibit. Many coating compositions known for their durability and/or weatherability when used in exterior paints, such as known high-solids enamels, do not provide the desired level of resistance to environmental etch when used in high gloss coatings such as the clearcoat of a color-plus-clear composite coating.

Various compositions have been proposed to meet the above requirements for use as the topcoat coating or as the clearcoat of a color-plus-clear composite coating, including polyurethanes, acid-epoxy systems and the like. However, many prior art systems suffer from disadvantages such as coatability problems, marginal compatibility with the pigmented basecoat, solubility problems, and marginal appearance. Moreover, while one-pack compositions are preferred to two-pack compositions (in which the reactive component must be separated before application to prevent premature reaction), very few one-pack coating compositions have been found that provide satisfactory resistance to environmental etch, especially in the demanding environment of automotive coatings.

In addition, it is desirable to provide coatings with a good combination of properties such as durability, hardness, flexibility, and resistance to scratching, marring, solvents, and acids.

Curable coating compositions utilizing carbamate-functional resins are described, for example, in U.S. Pat. Nos. 5,693,724, 5,693,723, 5,639,828, 5,512,639, 5,508,379, 5,451,656, 5,356,669, 5,336,566, and 5,532,061, each of which is incorporated herein by reference, and U.S. application Ser. Nos. 08/886,321, filed Jul. 1, 1997, 08/698,529, filed Aug. 15, 1996, 08/719,670, filed Sept. 25, 1996, 08/166,277, filed Dec. 13, 1993, 08/339,999, filed Nov. 15, 1994, 08/333,917, filed Nov. 3, 1994, 08/176,608, filed Jan. 3, 1994, 08/287,351, filed Aug. 8, 1994, 08/804,239, filed Feb. 20, 1997, 08/333,804, filed Nov. 3, 1994, 08.884,613, filed Jun. 30, 1997, 08/885,638, filed Jun. 30, 1997, 08/513, 587, filed Aug. 10, 1995, 08/867,547, filed Jun. 2, 1997, 08/547,514, filed Oct. 24, 1994, 08/547,513, filed Oct. 24, 1994, 08/547,174, filed Oct. 24, 1994, 08/698,524, filed Aug. 15, 1996, 08/698,526, filed Aug. 15, 1996, 08/667,261, filed Jun. 20, 1996, 08/698,528, filed Aug. 15, 1996, 08/698, 522, filed Aug. 15, 1996, 08/698,572, filed Aug. 15, 1996, 08/698,523, filed Aug. 15, 1996, 08/673,935, filed Jul. 1, 1996, 08/886,321, filed Jul. 1, 1997, and 08/831,810, filed Apr. 2, 1997, each of which is incorporated herein by reference. These coating compositions can provide significant etch advantages over other coating compositions, such as hydroxy-functional acrylic/melamine coating compositions. It may often be desirable, however, to provide still further improvements in the above-described coating properties.

SUMMARY OF THE INVENTION

The present invention provides a curable coating composition that includes at least three components: a component (a), a component (b), and a component (c).

First, the coating composition includes a component (a) having at least one carbamate group or urea group and having a lactone or hydroxy carboxylic acid moiety. When used in connection with the invention, the term "carbamate group" refers to a group having a structure

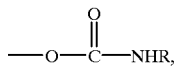

in which R is H or alkyl. Preferably, R is H or alkyl of from 1 to about 4 carbon atoms, and more preferably R is H. When used in connection with the invention, terminal urea group refers to a group having a structure

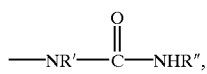

in which R' and R" are each independently H or alkyl, or R' and R" together form a heterocyclic ring structure. Preferably, R' and R" are each independently H or alkyl of from 1 to about 4 carbon atoms or together form an ethylene bridge, and more preferably R' and R" are each independently H. The terminal urea group of the invention is distinguished from urea linking groups for which R" would be other than alkyl.

Preferred compounds (a) may be represented by the structures

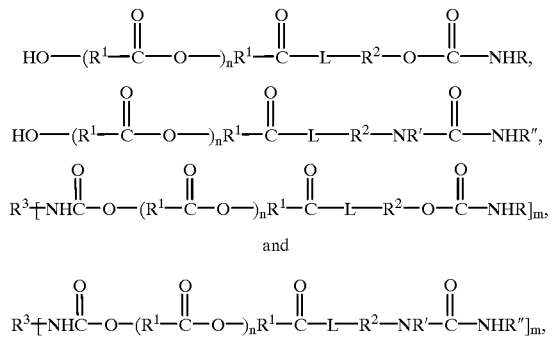

and in which R, R', and R" are as previously defined; R'' is alkylene or arylalkylene, preferably alkylene, and particularly alkylene of 5 to 10 carbon atoms; $R^2$ is alkylene or substituted alkylene, preferably having from about 2 to about 4 carbon atoms; $R^3$ is alkylene (including cycloalkylene), alkylarylene, arylene, or a structure that includes a cyanuric ring, a urethane group, a urea group, a carbodiimide group, a biuret structure, or an allophonate group, preferably alkylene (including cycloalkylene) or a structure that includes a cyanuric ring; n is from 0 to about 10, preferably from 0 to about 5; m is from 2 to about 6, preferably 2 or 3; and L is O, NH, or $NR^4$, where $R^4$ is an alkyl, preferably an alkyl of 1 to about 6 carbon atoms.

The compound (a) may be prepared by a process that involves a step of reacting together a lactone or a hydroxy carboxylic acid and a compound comprising a carbamate or urea group or a group that can be converted to a carbamate or urea group and a group that is reactive with the lactone or hydroxy carboxylic acid. In the case of a group that can be converted to a carbamate or urea group, the group is converted to the carbamate or urea group either during or after the reaction with the lactone or hydroxy carboxylic acid. The process for preparing compound (a) may include a further step in which a hydroxyl-functional product of the first step is reacted with a compound having at least two isocyanate groups.

The second component (b) of the coating composition is one or more of three materials. First, the second component can be a polymer resin (b)(1) comprising active hydrogen-containing functional groups reactive with the third component(c). Secondly, the second component can be a compound (b)(2) having at least one carbamate group or terminal urea group according to the invention and having at least two linking groups that are urethane or urea. Preferred compounds (b)(2) may be represented by any of the structures

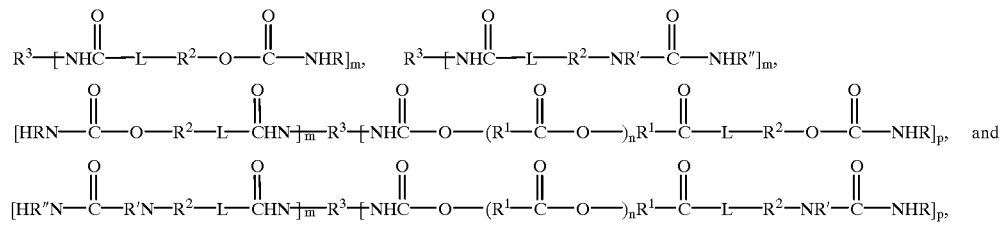

in which R, R', R'', $R^2_1$, $R^3$, L, and m are as previously defined; p is from 1 to 5, preferably 1 or 2, and m+p is 2 to 6, preferably about 3. Preferably, $R^3$ is alkylene (including cycloalkylene), alkylarylene, arylene, or a structure that includes a cyanuric ring.

The compound (b)(2) may be prepared by a process having a step of reacting together a polyisocyanate (b)(2)(B) and a compound (b)(2)(A) having a carbamate or terminal urea group or a group that can be converted to a carbamate or terminal urea group and also having a group that is reactive with isocyanate functionality. In the case of a group that can be converted to carbamate or terminal urea, the conversion to the carbamate or terminal urea group is carried out either at the same time as the reaction involving the polyisocyanate or afterwards to form the second component.

Finally, the second component can be a compound (b)(3) having at least two groups selected from carbamate groups, terminal urea groups, or combinations of the two and at least four urethane or urea linking groups. Preferred compounds (b)(3) may be represented by any of the structures

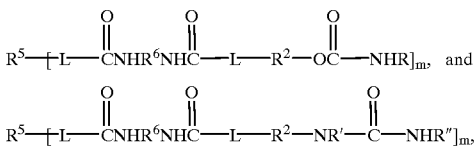

in which R, R', R", R², L, and m are as previously defined; R⁵ and R⁶ are each independently alkylene (including cycloalkylene), preferably having from 1 to about 18 carbon atoms, particularly preferably from about 5 to about 12 carbon atoms, alkylarylene, or arylene, or R⁶ is a structure that includes a cyanuric ring, a biuret structure, or an allophonate group.

The compound (b)(3) may be prepared by a synthesis that involves a step of reacting together a compound (b)(3)(A) comprising a carbamate or terminal urea group or a group that can be converted to a carbamate or terminal urea group and also having an isocyanate group and a compound (b)(3)(B) having at least two groups reactive with isocyanate functionality. When the compound (b)(3)(A) comprises a group that can be converted to a carbamate or terminal urea group, the conversion to carbamate or urea may take place at the same time as the reaction with the compound having at least two groups reactive with isocyanate functionality or after that reaction is completed, to generate the second component (b)(3).

The third component (c) of the coating composition is a curing agent that is reactive with the first two components.

The invention further provides an article having a substrate, in particular a flexible substrate, upon which substrate is a cured coating derived from a coating composition according to the invention and a method of producing such a coating on a substrate.

DETAILED DESCRIPTION

The composition according to the present invention includes as a first component a compound (a) having at least one carbamate group or terminal urea group and having a lactone or hydroxy acid moiety. By "lactone or hydroxy acid moiety" it is meant a structure resulting from incorporation of a lactone or hydroxy acid into the compound. For example, a lactone or hydroxy acid could be incorporated into compound (a) as an ester or polyester segment by reaction with a hydroxyl or a primary or secondary amine group on compound (a). Preferred compounds (a) may be represented by the structures

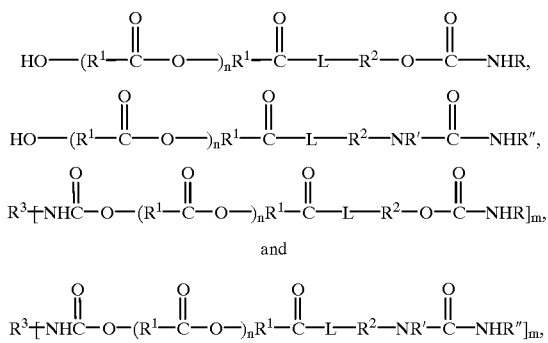

in which R, R', and R" are as previously defined; R¹ is alkylene or arylalkylene, preferably alkylene, and particularly alkylene of 5 to 10 carbon atoms; R² is alkylene or substituted alkylene, preferably having from about 2 to about 4 carbon atoms; R³ is alkylene (including cycloalkylene), alkylarylene, arylene, or a structure that includes a cyanuric ring, a urethane group, a urea group, a carbodiimide group, a biuret structure, or an allophonate group, preferably alkylene (including cycloalkylene) or a structure that includes a cyanuric ring; n is from 0 to about 10, preferably from 0 to about 5; m is from 2 to about 6, preferably 2 or 3; and L is O, NH, or NR⁴, where R⁴ is an alkyl, preferably an alkyl of 1 to about 6 carbon atoms.

The compound (a) may be prepared by a process that involves a step of reacting together a lactone or a hydroxy carboxylic acid and a compound (a)(1) comprising a carbamate or terminal urea group or a group that can be converted to a carbamate or terminal urea group and a group that is reactive with the lactone or hydroxy carboxylic acid. Preferably, the compound (a)(1) has a carbamate or terminal urea group or, in an alternative preferred embodiment, it has a carbamate group or a group that can be converted to a carbamate group. In a particularly preferred embodiment, the compound (a)(1) has a carbamate group.

Suitable functional groups reactive with the lactone or hydroxyl carboxylic acid include, without limitation, hydroxyl groups, carboxyl groups, isocyanate groups, and primary and secondary amine groups. Preferably, the compound (a)(1) has a hydroxyl group or an amino group as the group reactive with the lactone or hydroxyl carboxylic acid. The compound (a)(1) has at least one group that is reactive with the lactone or hydroxy carboxylic acid, and preferably it has from 1 to about 3 of such groups, and more preferably it has one such reactive group. In a preferred embodiment, the compound (a)(1) has a carbamate group and a hydroxyl group. One preferred example of such a compound is a hydroxyalkyl carbamate, particularly a β-hydroxyalkyl carbamate. In another preferred embodiment, the compound (a)(1) has a terminal urea group and a hydroxyl group.

Suitable compounds (a)(1) include, without limitation, any of those compounds having a carbamate or terminal urea group and a group reactive with lactone or hydroxyl carboxylic acid that are known in the art. Hydroxypropyl carbamate and hydroxyethyl ethylene urea, for example, are well known and commercially available. Amino carbamates are described in U.S. Pat. No. 2,842,523. Hydroxyl ureas may also be prepared by reacting the amine group of an amino alcohol with hydrochloric acid and then urea to form a hydroxy urea compound. An amino alcohol can be prepared, for example, by reacting an oxazolidone with ammonia. Amino ureas can be prepared, for example, by reacting a ketone with a diamine having one amine group protected from reaction (e.g., by steric hindrance), followed by reaction with HNCO (e.g., as generated by thermal decomposition of urea), and finally reaction with water. Alternatively, these compounds can be prepared by starting with a compound having the group that can be converted to carbamate or terminal urea, which groups are described below, and converting that group to the carbamate or urea prior to beginning the reaction with the lactone or hydroxy carboxylic acid.

In another aspect of the invention, the preparation of compound (a) includes a further step in which the product of the reaction of compound (a)(1) is reacted with the lactone or carboxylic acid with a polyisocyanate. Preferably, the product of compound (a)(1) and the lactone or hydroxy carboxylic acid has a hydroxyl group at the end of the lactone or hydroxy carboxylic acid segment that is reacted with the polyisocyanate. Suitable examples of polyisocyanate compounds include both aliphatic polyisocyanates and aromatic polyisocyanates. Useful polyisocyanates include monomeric isocyanates, for example aliphatic diisocyanates such as ethylene diisocyanate, 1,2-diisocyanatopropane, 1,3-diisocyanatopropane, 1,6-diisocyanatohexane (hexamethylene diisocyanate or HMDI), 1,4-butylene diisocyanate, lysine diisocyanate, 1,4-methylene bis-(cyclohexyl isocyanate) and isophorone diisocyanate (IPDI), and aromatic diisocyanates and arylaliphatic diisocyanates such as the various isomers of toluene diisocyanate, meta-xylylenediioscyanate and para-xylylenediisocyanate, 4-chloro-1,3-phenylene diisocyanate, 1,5-tetrahydro-naphthalene diisocyanate, 4,4'-dibenzyl diisocyanate, and 1,2,4-benzene triisocyanate. In addition, the various isomers of $\alpha$, $\alpha,\alpha'$, $\alpha'$-tetramethyl xylylene diisocyanate can be used. Isocyanate-functional oligomers or low molecular weight reaction products of the monomeric isocyanates, which may have from 2 to about 6 isocyanate groups, may also be used. Examples of these include isocyanurates and the reaction products of excess isocyanate with polyols, such as the product of three moles of diisocyanate with a mole of a triol (e.g., 3 moles of IPDI with one mole of trimethylolpropane or two moles of IPDI with one mole of neopentyl glycol); reaction products of isocyanate with urea (biurets); and reaction products of isocyanate with urethane (allophanates). The polyisocyanate preferably has two to four isocyanate groups, and more preferably the polyisocyanate has 2 or 3 isocyanate groups per molecule. Isocyanurates such as the isocyanurates of isophorone diisocyanate or hexamethylene diisocyanate are particularly preferred. In a particularly preferred embodiment, a $\beta$-hydroxyalkyl carbamate is reacted with epsilon-caprolactone and the product of this reaction is then reacted with a polyisocyanate, preferably the isocyanurate of IPDI. It should be appreciated that the order of the various reaction steps may in many cases be varied in the synthesis of the compounds of the invention.

When a compound (a)(1) that has a group that can be converted to carbamate or terminal urea is used, conversion of the group to a carbamate or urea can be accomplished during or after the reaction with the lactone or the hydroxy carboxylic acid to produce the first component. Groups that can be converted to carbamate include cyclic carbonate groups, epoxy groups, and unsaturated bonds. Cyclic carbonate groups can be converted to carbamate groups by reaction with ammonia or a primary amine, which ring-opens the cyclic carbonate to form a $\beta$-hydroxy carbamate. Epoxy groups can be converted to carbamate groups by first converting to a cyclic carbonate group by reaction with $CO_2$. This can be done at any pressure from atmospheric up to supercritical $CO_2$ pressures, but is preferably under elevated pressure (e.g., 60–150 psi). The temperature for this reaction is preferably 60–150° C. Useful catalysts include any that activate an oxirane ring, such as tertiary amine or quaternary salts (e.g., tetramethyl ammonium bromide), combinations of complex organotin halides and alkyl phosphonium halides (e.g., $(CH_3)_3SnI$, $Bu_4SnI$, $Bu_4PI$, and $(CH_3)_4PI$), potassium salts (e.g., $K_2CO_3$, KI) preferably in combination with crown ethers, tin octoate, calcium octoate, and the like. The cyclic carbonate group can then be converted to a carbamate group as described above. Any unsaturated bond can be converted to a carbamate group by first reacting with peroxide to convert to an epoxy group, then with $CO_2$ to form a cyclic carbonate, and then with ammonia or a primary amine to form the carbamate.

Other groups, such as hydroxyl groups or isocyanate groups can also be converted to carbamate groups. However, if such groups were to be present on the compound (a)(1) and it is desired to convert those groups to carbamate after the reaction with the lactone or hydroxycarboxylic acid, they would have to be blocked or protected so that they would not react during the lactone reaction. When blocking these groups is not feasible, the conversion to carbamate or terminal urea would have to be completed prior to the lactone reaction. Hydroxyl groups can be converted to carbamate groups by reaction with a monoisocyanate (e.g., methyl isocyanate) to form a secondary carbamate group (that is, a carbamate of the structure above in which R is alkyl) or with cyanic acid (which may be formed in situ by thermal decomposition of urea) to form a primary carbamate group (i.e., R in the above formula is H). This reaction preferably occurs in the presence of a catalyst as is known in the art. A hydroxyl group can also be reacted with phosgene and then ammonia to form a primary carbamate group, or by reaction of the hydroxyl with phosgene and then a primary amine to form a compound having secondary carbamate groups. Another approach is to react an isocyanate with a compound such as hydroxyalkyl carbamate to form a carbamate-capped isocyanate derivative. For example, one isocyanate group on toluene diisocyanate can be reacted with hydroxypropyl carbamate, followed by reaction of the other isocyanate group with an excess of polyol to form a hydroxy carbamate. Finally, carbamates can be prepared by a transesterification approach where a hydroxyl group is reacted with an alkyl carbamate (e.g., methyl carbamate, ethyl carbamate, butyl carbamate) to form a primary carbamate group-containing compound. This reaction is performed at elevated temperatures, preferably in the presence of a catalyst such as an organometallic catalyst (e.g., dibutyltin dilaurate). Other techniques for preparing carbamates are also known in the art and are described, for example, in P. Adams & F. Baron, "Esters of Carbamic Acid", *Chemical Review*, v. 65, 1965 and in U.S. Pat. No. 5,474,811, issued to Rehfuss and St. Aubin.

Groups such as oxazolidone can also be converted to terminal urea after reaction with the lactone or hydroxy carboxylic acid. For example, hydroxyethyl oxazolidone can be used to react with the lactone or hydroxy carboxylic acid, followed by reaction of ammonia or a primary amine with the oxazolidone to generate the urea functional group.

One preferred class of compounds (a)(1) having a group reactive with the lactone or hydroxy carboxylic acid and a group that can be converted to carbamate is the hydroxyalkyl cyclic carbonates. Hydroxyalkyl cyclic carbonates can be prepared by a number of approaches. Certain hydroxyalkyl cyclic carbonates like 3-hydroxypropyl carbonate (i.e., glycerine carbonate) are commercially available. Cyclic carbonate compounds can be synthesized by any of several different approaches. One approach involves reacting an epoxy group-containing compound with $CO_2$ under conditions and with catalysts as described hereinabove. Epoxides can also be reacted with $\beta$-butyrolactone in the presence of such catalysts. In another approach, a glycol like glycerine is reacted at temperatures of at least 80° C. with diethyl carbonate in the presence of a catalyst (e.g., potassium carbonate) to form a hydroxyalkyl carbonate. Alternatively, a functional compound containing a ketal of a 1,2-diol having the structure:

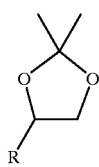

can be ring-opened with water, preferably with a trace amount of acid, to form a 1,2-glycol, the glycol then being further reacted with diethyl carbonate to form the cyclic carbonate.

Cyclic carbonates typically have 5- or 6-membered rings, as is known in the art. Five-membered rings are preferred, due to their ease of synthesis and greater degree of commercial availability. Six-membered rings can be synthesized by reacting phosgene with 1,3-propanediol under conditions known in the art for the formation of cyclic carbonates. Preferred hydroxyalkyl cyclic carbonates used in the practice of the invention can be represented by the formula:

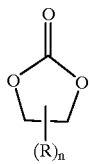

in which R (or each instance of R if n is more than 1) is a hydroxyalkyl group of 1–18 carbon atoms, preferably 1–6 carbon atoms, and more preferably 1–3 carbon atoms, which may be linear or branched and may have substituents in addition to the hydroxyl group, and n is 1 or 2, which may be substituted by one or more other substituents such as blocked amines or unsaturated groups. The hydroxyl group may be on a primary, secondary, or tertiary carbon. More preferably, R is —$(CH_2)_p$—OH, where the hydroxyl may be on a primary or secondary carbon and p is 1 to 8, and even more preferably in which the hydroxyl is on a primary carbon and p is 1 or 2.

The compound (a)(2) may be a lactone or a hydroxy carboxylic acid. Lactones that can be ring opened by an active hydrogen are well-known in the art. They include, for example, ε-caprolactone, γ-caprolactone, β-butyrolactone, β-propriolactone, γ-butyrolactone, α-methyl-γ-butyrolactone, β-methyl-γ-butyrolactone, γ-valerolactone, δ-valerolactone, γ-nonanoic lactone, γ-octanoic lactone, and pentolactone. In one preferred embodiment, the lactone is ε-caprolactone. Lactones useful in the practice of the invention can also be characterized by the formula:

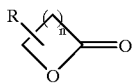

wherein n is a positive integer of 1 to 7 and R is one or more H atoms, or substituted or unsubstituted alkyl groups of 1–7 carbon atoms.

The lactone ring-opening reaction is typically conducted under elevated temperature (e.g., 80–150° C.). The reactants are usually liquids so that a solvent is not necessary. However, a solvent may be useful in promoting good conditions for the reaction even if the reactants are liquid. Any non-reactive solvent may be used, including both polar and nonpolar organic solvents. Examples of useful solvents include toluene, xylene, methyl ethyl ketone, methyl isobutyl ketone, and the like. A catalyst is preferably present. Useful catalysts include proton acids (e.g., octanoic acid, Amberlyst® 15 (Rohm & Haas)), and tin catalysts (e.g., stannous octoate). Alternatively, the reaction can be initiated by forming a sodium salt of the hydroxyl group on the molecules that react will react with the lactone ring.

A hydroxy carboxylic acid can also be used as compound (a)(2). Useful hydroxy carboxylic acids include dimethylhydroxypropionic acid, hydroxy stearic acid, tartaric acid, lactic acid, 2-hydroxyethyl benzoic acid, and N-(2-hydroxyethyl)ethylene diamine triacetic acid. The reaction can be conducted under typical esterification conditions, for example at temperatures from room temperature up to about 150° C., and with catalysts such as calcium octoate, metal hydroxides like potassium hydroxide, Group I or Group II metals such as sodium or lithium, metal carbonates such as potassium carbonate or magnesium carbonate (which may be enhanced by use in combination with crown ethers), organometallic oxides and esters such as dibutyl tin oxide, stannous octoate, and calcium octoate, metal alkoxides such as sodium methoxide and aluminum tripropoxide, protic acids like sulfuric acid, or $Ph_4SbI$. The reaction may also be conducted at room temperature with a polymer-supported catalyst such as Amerlyst-15® (available from Rohm & Haas) as described by R. Anand in Synthetic Communications, 24(19), 2743–47 (1994), the disclosure of which is incorporated herein by reference. The reaction may be performed with an excess of the compound having the group reactive with the hydroxy carboxylic acid.

The reaction with the compound (a)(2) can provide chain extension of the compound (a)(1) molecule if sufficient amounts of the compound (a)(2) are present. The relative amounts of the (a)(1) compound and the (a)(2) lactone and/or hydroxy acid can be varied to control the degree of chain extension. The reaction of the lactone ring or of the hydroxy carboxylic acid with a hydroxyl or amine group results in the formation of an ester or amide and an OH group. The resulting OH group can then react with another available lactone ring or molecule of hydroxy carboxylic acid, thus resulting in chain extension. The reaction is thus controlled by the proportion of the compound(s) (a)(2) to the amount of initiator compound (a)(1). In the preferred embodiments of the present invention, the ratio of equivalents of lactone and/or hydroxy carboxylic acid to equivalents of active hydrogen groups on compound (a)(1) is preferably from 0.1:1 to 10:1, and more preferably from 1:1 to 5:1. When the reaction product has an acid group, the acid group can then be converted to a hydroxyl group by well-known techniques such as reaction with ethylene oxide.

The second component (b) of the coating compositions of the invention may be one or more of three materials. First, the second component can be a oligomeric or polymeric resin (b)(1) comprising active hydrogen-containing functional groups that are reactive with the third component curing agent (c). Suitable active hydrogen-containing functional groups include, without limitation, hydroxyl functionality, acid functionality, carbamate functionality, urea functionality, and combinations of these. The polymer resin (b)(1) preferably has, on average, at least two reactive-hydrogen containing functional groups per molecule, although, depending upon the type of polymer, the average number of functional groups per molecule may be much higher. The preferred number of functional groups per molecule in a particular case will depend not only upon the type of polymer, but also upon the functionality of the crosslinker or curing agent (c), the desired crosslink density, and other factors typically considered in formulating coating compositions. In a preferred embodiment, the polymer (b)(1) has carbamate or terminal urea functionality. The carbamate or terminal urea functionality may be introduced to the polymer by either polymerizing using a carbamate- or terminal urea-functional monomer or by reacting a functional group on the formed polymer in a further reaction to produce a carbamate or terminal urea functionality at that position. If the functional group on the polymer (b)(1) is an isocyanate group, the group can be reacted with a hydroxyalkyl carbamate, or with a hydroxy-containing epoxide with the epoxy group subsequently converted to carbamate by reaction with $CO_2$ and then ammonia. Preferably, an isocyanate-functional polymer is reacted with hydroxyethyl carbamate, hydroxypropyl carbamate, hydroxybutyl carbamate, or mixtures thereof. If the functional group is hydroxyl, the reactive group on the carbamate-containing compound may be oxygen of the $C(=O)O$ portion of the carbamate group on an alkyl carbamate or methylol, such as with methylol acrylamide ($HO-CH_2-NH-C(=O)-CH=CH_2$). In the case of the $C(=O)O$ group on an alkyl carbamate, the hydroxyl group on the polymer undergoes a transesterification with the $C(=O)O$ group, resulting in the carbamate group being appended to the polymer. In the case of methylol acrylamide, the unsaturated double bond is then reacted with peroxide, $CO_2$, and ammonia as described above. If the functional group on the polymer is a carboxyl group, the acid group can be reacted with epichlorohydrin to form a monoglycidyl ester, which can be converted to carbamate by reaction with $CO_2$, and then ammonia.

Carbamate functionality can be introduced to the polymer (b)(1) by reacting the polymer with a compound that has a group that can be converted to a carbamate, and then converting that group to the carbamate. Examples of suitable compounds with groups that can be converted to a carbamate include active hydrogen-containing cyclic carbonate compounds (e.g., the reaction product of glycidol and $CO_2$) that are convertible to carbamate by reaction with ammonia, monoglycidyl ethers and esters convertible to carbamate by reaction with $CO_2$ and then ammonia, allyl alcohols where the alcohol group is reactive with isocyanate functionality and the double bond can be converted to carbamate by reaction with peroxide, and vinyl esters where the ester group is reactive with isocyanate functionality and the vinyl group can be converted to carbamate by reaction with peroxide, then $CO_2$, and then ammonia. Any of the above compounds can be utilized as compounds containing carbamate groups rather than groups convertible to carbamate by converting the group to carbamate prior to reaction with the polymer.

In general, the polymer (b)(1) can be of the type normally utilized for thermosetting coating compositions, such as acrylic resins, vinyl resins, alkyds, polyesters, polyurethanes, polyester-polyurethane copolymers, modified acrylic polymers, polyepoxides, polycarbonates, polyamides, polyimides, and polysiloxanes, and so on. In particular for automotive topcoat coating compositions (including basecoat and clearcoat coating compositions), acrylic resins, polyester resins, polyurethane resins, and polyester-polyurethane copolymers are preferred. More preferably, the resin is an acrylic resin.

The acrylic resin preferably has a molecular weight of 500 to 1,000,000, and more preferably of 1500 to 50,000. As used herein, "molecular weight" refers to number average molecular weight, which may be determined by the GPC method using a polystyrene standard. Such polymers can be prepared from acrylic monomers such as methyl acrylate, acrylic acid, methacrylic acid, methyl methacrylate, butyl methacrylate, cyclohexyl methacrylate, and the like. The functional group can be incorporated into the ester portion of the acrylic monomer. For example, hydroxy-functional acrylic monomers that can be used to form such polymers include hydroxyethyl acrylate, hydroxybutyl acrylate, hydroxybutyl methacrylate, hydroxypropyl acrylate, and the like; amino-functional acrylic monomers would include t-butylaminoethyl methacrylate and t-butylaminoethylacrylate; acid-functional monomers would include acrylic acid, methacrylic acid, and itaconic acid; epoxide-functional monomers would include glycidyl acrylate and glycidyl methacrylate; and so on.

Modified acrylics can also be used as the polymer (b)(1) according to the invention. Such acrylics may be polyester-modified acrylics or polyurethane-modified acrylics, as is well-known in the art. Polyester-modified acrylics modified with ε-caprolactone are described in U.S. Pat. No. 4,546,046 of Etzell et al., the disclosure of which is incorporated herein by reference. Polyurethane-modified acrylics are also well-known in the art. They are described, for example, in U.S. Pat. No. 4,584,354, the disclosure of which is incorporated herein by reference.

In one embodiment, the second component (b) may include a carbamate-functional acrylic resin or polymer. A carbamate-functional resin or polymer can be prepared in a variety of ways. One way to prepare such polymers is to prepare an acrylic monomer having a carbamate functionality in the ester portion of the monomer. Such monomers are well-known in the art and are described, for example in U.S. Pat. Nos. 3,479,328, 3,674,838, 4,126,747, 4,279,833, and 4,340,497, 5,356,669, and WO 94/10211, the disclosures of which are incorporated herein by reference. One method of synthesis involves reaction of a hydroxy-functional monomer with cyanic acid (which may be formed by the thermal decomposition of urea) to form the carbamyloxy carboxylate (i.e., carbamate-modified (meth)acrylate). Another method of synthesis reacts an α, β-unsaturated acid ester with a hydroxy carbamate ester to form the carbamyloxy carboxylate. Yet another technique involves formation of a hydroxyalkyl carbamate by reacting a primary or secondary amine or diamine with a cyclic carbonate such as ethylene carbonate. The hydroxyl group on the hydroxyalkyl carbamate is then esterified by reaction with acrylic or methacrylic acid to form the monomer. Other methods of preparing carbamate-modified acrylic monomers are described in the art, and can be utilized as well. The acrylic monomer can then be polymerized along with other ethylenically-unsaturated monomers, if desired, by techniques well-known in the art.

An alternative-route for preparing a carbamate-functional polymer is to react an already-formed polymer such as an acrylic polymer with another component to form a carbamate-functional group appended to the polymer backbone, as described in U.S. Pat. No. 4,758,632, the disclosure of which is incorporated herein by reference. One technique for preparing acrylic polymers useful as the second component involves thermally decomposing urea (to give off ammonia and HNCO) in the presence of a hydroxy-functional acrylic polymer to form a carbamate-functional acrylic polymer. Another technique involves reacting the hydroxyl group of a hydroxyalkyl carbamate with the isocyanate group of an isocyanate-functional acrylic or vinyl monomer to form the carbamate-functional acrylic. Isocyanate-functional acrylics are known in the art and are described, for example in U.S. Pat. No. 4,301,257, the disclosure of which is incorporated herein by reference.

Isocyanate vinyl monomers are well-known in the art and include unsaturated m-tetramethyl xylene isocyanate and isocyanatoethyl methacrylate. Yet another technique is to react the cyclic carbonate group on a cyclic carbonate-functional acrylic with ammonia in order to form the carbamate-functional acrylic. Cyclic carbonate-functional acrylic polymers are known in the art and are described, for example, in U.S. Pat. No. 2,979,514, the disclosure of which is incorporated herein by reference. Another technique is to transcarbamylate a hydroxy-functional acrylic polymer with an alkyl carbamate. A more difficult, but feasible way of preparing the polymer would be to trans-esterify an acrylate polymer with a hydroxyalkyl carbamate.

A carbamate-functional addition polymer component can be represented by the randomly repeating units according to the following formula:

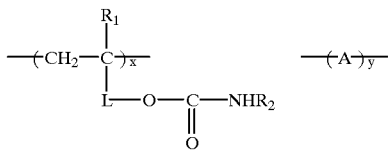

In the above formula, $R_1$ represents H or $CH_3$. $R_2$ represents H, alkyl, preferably of 1 to 6 carbon atoms, or cycloalkyl, preferably up to 6 ring carbon atoms. It is to be understood that the terms alkyl and cycloalkyl are to include substituted alkyl and cycloalkyl, such as halogen-substituted alkyl or cycloalkyl. Substituents that will have an adverse impact on the properties of the cured material, however, are to be avoided. For example, ether linkages are thought to be susceptible to hydrolysis, and should be avoided in locations that would place the ether linkage in the crosslink matrix. The values x and y represent weight percentages, with x being 10 to 90% and preferably 40 to 60%, and y being 90 to 10% and preferably 60 to 40%.

In the formula, A represents polymerized units derived from one or more ethylenically unsaturated co-monomers. Such monomers for copolymerization are known in the art. They include alkyl esters of acrylic or methacrylic acid, e.g., ethyl acrylate, butyl acrylate, 2-ethylhexyl acrylate, butyl methacrylate, isodecyl methacrylate, hydroxyethyl methacrylate, hydroxypropyl acrylate, and the like; and vinyl monomers such as unsaturated m-tetramethyl xylene isocyanate, styrene, vinyl toluene and the like. Suitable co-monomers also include monomer having other functionalities, including hydroxyl, acid, and epoxide functionalities.

L represents a divalent linking group, preferably an aliphatic of 1 to 8 carbon atoms, cycloaliphatic, or aromatic linking group of 6 to 10 carbon atoms. Examples of L include

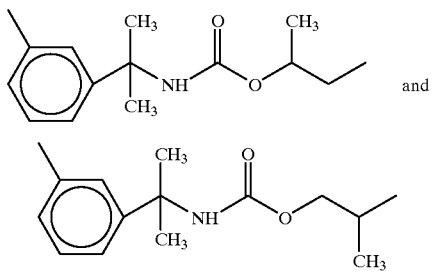

$-(CH_2)-$, $-(CH_2)_2-$, $-(CH_2)_4-$, and the like. In one preferred embodiment, $-L-$ is represented by $-COO-L'-$ where L' is a divalent linking group. Thus, in a preferred embodiment of the invention, the polymer component (a) is represented by randomly repeating units according to the following formula:

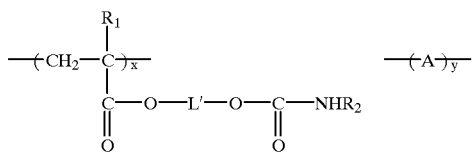

In this formula, $R_1$, $R_2$, A, x, and y are as defined above. L' may be a divalent aliphatic linking group, preferably of 1 to 8 carbon atoms, e.g., $-(CH_2)-$, $-(CH_2)_2-$, $-(CH_2)_4-$, and the like, or a divalent cycloaliphatic linking group, preferably up to 8 carbon atoms, e.g., cyclohexyl, and the like. However, other divalent linking groups can be used, depending on the technique used to prepare the polymer. For example, if a hydroxyalkyl carbamate is adducted onto an isocyanate-functional acrylic polymer, the linking group L' would include an $-NHC(=O)O-$ urethane linkage as a residue of the isocyanate group.

Polyesters having epoxide groups or active hydrogen groups such as hydroxyl groups, acid groups, or carbamate groups that are reactive with the curing agent third component (c) can also be used as the polymer (b)(1) in the composition according to the invention. Such polyesters may be prepared by the polyesterification of organic polycarboxylic acids (e.g., phthalic acid, hexahydrophthalic acid, adipic acid, maleic acid) or their anhydrides with organic polyols (e.g., ethylene glycol, butylene glycol, neopentyl glycol). Hydroxyl or carboxyl functional polyesters are prepared by including an excess of the polyol or polyacid monomer. In a preferred embodiment, the polymer (b)(1) is a polyester resin or polyester-polyurethane copolymer resin having a structural moiety resulting from a ring-opening reaction of a lactone or reaction of a hydroxy acid. Preparation of such resins involves reaction of lactone and/or hydroxy acid with an active-hydrogen containing monomer during or after polyester synthesis. In one preferred embodiment, a polyol, preferably a diol, is extended with a lactone, preferably with ε-caprolactone, to form an hydroxyl-functional polyester. In another preferred synthesis, a hydroxy-functional polyester resin is reacted with a lactone or hydroxycarboxylic acid after the polymerization reaction.

Carbamate functionality may be introduced to the polyester by suitable methods already described. Carbamate-functional polyesters are disclosed in U.S. Pat. Nos. 5,508,379, 5,451,656, and 5,532,061, the disclosures of each of which is incorporated herein by reference. The polyester formed from lactone and/or hydroxy acid may similarly have a carbamate group introduced.

The polymer or resin (b)(1) used as the second component (b) may be a polyurethane having any of the active hydrogen-containing functional groups mentioned above for the polymer (b)(1). Synthesis of polyurethanes, particularly hydroxy-functional polyurethanes, is well-known in the art. In general, polyurethanes are prepared by reaction of a polyisocyanate component with a polyol component. Preferably, the polyurethane is linear (that is, it is prepared by reacting one or more diisocyanates with one or more diols). Hydroxyl functional polyurethanes may be prepared by reaction an excess of equivalents of diol with diisocyanate(s). Hydroxyl-functional or amine-functional polyurethanes may also be prepared by reacting an isocyanate-terminated polyurethane with an excess of equivalents of a diol, polyol, polyamine, or amino alcohol (such as diethanol amine) in a capping step. Acid-functional polyurethanes may be synthesized by including a monomer having acid functionality, such as, without limitation, dimethylolpropionic acid. The hydroxyl groups react to form the urethane linkages while the acid group remains unreacted in the polyurethane polymerization. Carbamate- or terminal urea-functional polyurethanes can be prepared by reacting an NCO-terminated polyurethane with a hydroxy carbamate (e.g., hydroxypropyl carbamate) or a hydroxy urea (e.g., hydroxyethyl ethylene urea) using techniques described as above and in U.S. Pat. No. 5,373,069 or by including a carbamate or urea diol (which may be formed by ring-opening a hydroxyalkyl cyclic carbonate or a hydroxyalkyl oxazolidone with ammonia or a primary amine).

Preparation of polyurethanes for coating compositions are described in many publications. In general, monomeric polyisocyanates such as those mentioned already may be used in preparing the polyurethane. Aliphatic diisocyanates, particularly IPDI, are preferred. Useful active hydrogen-containing chain extension agents generally contain at least two active hydrogen groups, for example, diols, dithiols, diamines, or compounds having a mixture of hydroxyl, thiol, and amine groups, such as alkanolamines, aminoalkyl mercaptans, and hydroxyalkyl mercaptans, among others. For purposes of this aspect of the invention both primary and secondary amine groups are considered as having one active hydrogen. Active hydrogen-containing chain extension agents also include water. In a preferred embodiment of the invention, a polyol is used as the chain extension agent. In an especially preferred embodiment, a diol is used as the chain extension agent with little or no higher polyols, so as to minimize branching. Examples of preferred diols that are used as polyurethane chain extenders include, without limitation, 1,6-hexanediol, cyclohexanedimethanol (sold as CHDM by Eastman Chemical Co.), 2-ethyl-1,6-hexanediol, 3-hydroxy-2,2-dimethylpropyl 3-hydroxy-2,2-dimethylpropionate (sold by Eastman Chemical Co. as Esterdiol 204), and 1,4-butanediol. While polyhydroxy compounds containing at least three hydroxyl groups may be used as chain extenders, the use of these compounds produces branched polyurethane resins. These higher functional polyhydroxy compounds include, for example, trimethylolpropane, trimethylolethane, pentaerythritol, among other compounds. Polymeric chain extension agents can also be used, such as polyester polyols, polyether polyols, polyurethane polyols, or polymeric amino group-containing polymers, and it is often preferred to include these. Mixtures of any of the above chain extension agents can also be used. In a preferred embodiment, a polyester polyol is included, in particular a polyester that is the reaction product of caprolactone with a diol.

The reaction of the polyisocyanate and chain extension agent is conducted by heating the components in a suitable reaction medium such as xylene or propylene glycol monoethylether acetate. The use of catalysts for this reaction, e.g., organotin catalysts such as dibutyltin diacetate, is well-known in the art. Polyurethanes useful as the (b)(1) component may have a number average molecular weight of from 600 to 6000. Various groups, such as nonionic polyether stabilizing groups, ionic stabilizing groups (e.g., carboxyl groups), unsaturated groups, and the like may be incorporated or appended to the material, as is known in the art. Active hydrogen or isocyanate terminal groups may be provided by adjusting the stoichiometry of the chain extension agent and polyisocyanate in the reaction mixture. A molar ratio of active hydrogen:NCO in the reaction mixture of less than 1 will tend to provide isocyanate-terminated polymers. Other terminal groups may be provided by the use of capping agents. For example, an acid terminal group can be provided by capping an isocyanate-terminated polymer with a hydroxyacid. Pendant functional groups may be provided by using chain extension agents having two active hydrogen groups and the desired functional group, e.g., dimethanol propionic acid, as noted above.

Secondly, the component (b) may also include, instead of the polymer (b)(1) or in addition to the polymer (b)(1) just described, a compound (b)(2) having at least one carbamate group or terminal urea group and having at least two linking groups that are urethane or urea. Preferred compounds (b)(2) may be represented by any of the structures

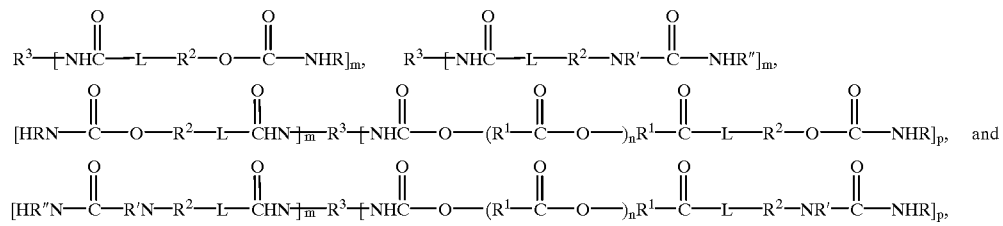

in which R, R', R", $R^2$, $R^3$, L, and m are as previously defined; p is from 1 to 5, preferably 1 or 2, and m+p is 2 to 6, preferably about 3. Preferably, $R^3$ is alkylene (including cycloalkylene), alkylarylene, arylene, or a structure that includes a cyanuric ring. In one preferred embodiment $R^3$ includes a member selected from the group of

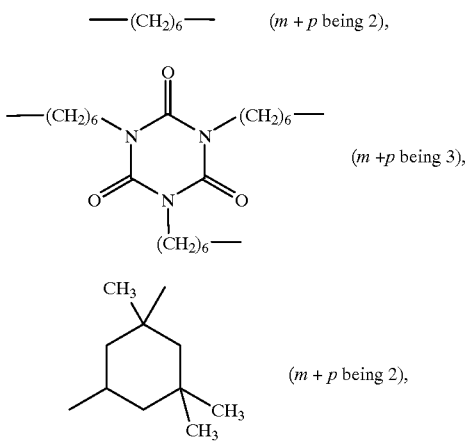

-continued

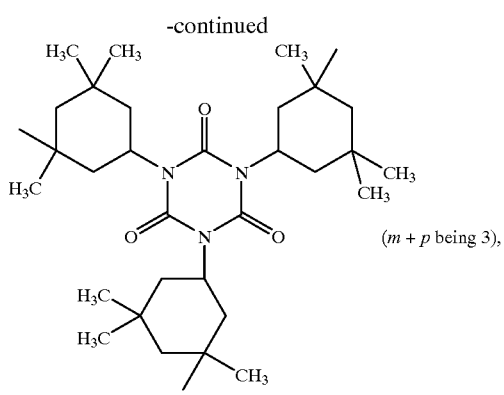

(m + p being 3), and mixtures thereof. L is particularly preferably an oxygen atom.

The compound of (b)(2) may be prepared by a step of reacting a mixture that includes at least a polyisocyanate (b)(2)(B) and a compound (b)(2)(A) having a carbamate or terminal urea group as defined for the invention or a group that can be converted to a carbamate or terminal urea group and also having a group that is reactive with isocyanate functionality. The polyisocyanate (b)(2)(B) may be, for example, any of the aforementioned polyisocyanate compounds. In one preferred embodiment, the polyisocyanate (b)(2)(B) is isophorone diisocyanate, the isocyanurate of isophorone diisocyanate, hexamethylene diisocyanate, the isocyanurate of isophorone diisocyanate, or a combination of these. In another preferred embodiment, the polyisocyanate is an isocyanate-functional monomeric or oligomeric, preferably monomeric, reaction product of a diisocyanate and a polyol. Such a reaction product may prepared by reacting one mole of a diisocyanate per equivalent of polyol. This endcapping is preferably accomplished by reacting at least two equivalents of isocyanate of a diisocyanate for each equivalent of hydroxyl of the polyol. The diisocyanate is preferably isophorone diisocyanate or hexamethylene diisocyanate. The polyol is preferably 2-ethyl-1,6-hexanediol, trimethylolpropane, neopentyl glycol, or a combination of these.

Carbamate groups, terminal urea groups, and groups convertible to carbamate or terminal urea groups have also been described. Groups reactive with isocyanate functionality include, without limitation, hydroxyl groups, primary amine groups, and secondary amine groups. Hydroxyl groups are preferred. Examples of compounds (b)(2)(A) having urea groups, carbamate groups, or groups convertible to carbamate or urea groups as well as hydroxyl or amino groups have already been mentioned. For example, an isocyanate (preferably a diisocyanate, e.g., HDI, IPDI, or the isocyanate-functional endcapped polyol described in the previous paragraph) may be reacted with a compound such as hydroxypropyl carbamate to form a carbamate-capped polyisocyanate derivative as described in U.S. Pat. No. 5,512,639.

The reaction mixture that includes at least a polyisocyanate (b)(2)(B) and a compound (b)(2)(A) having a carbamate or urea group or a group that can be converted to a carbamate or urea group and also having a group that is reactive with isocyanate functionality may further include an active-hydrogen chain extension compound, such as any of those described above in connection with the polyurethane.

In one embodiment of the invention, the (b)(2)(A) compound may be a hydroxyalkyl carbamate such as hydroxypropyl carbamate or hydroxyethyl carbamate. Alternatively, the compound (b)(2)(A) may have a group capable of forming a carbamate group after reaction with the (b)(2)(B) polyisocyanate such as compounds (b)(2)(B) having an active hydrogen group (e.g., hydroxyl) and a cyclic carbonate group (e.g., the reaction product of glycidol and $CO_2$). As already described, cyclic carbonate groups can be reacted with ammonia to form the carbamate functional groups. In another embodiment, the polyisocyanate can be reacted with a compound having an active hydrogen group (e.g., hydroxyl) and an epoxy group, and then with $CO_2$ to convert the epoxy to cyclic carbonate, and the cyclic carbonate groups then reacted with ammonia to form the carbamate functional groups.

Another method of synthesis is to first react the isocyanate groups on the polyisocyanate with a compound having a group that is reactive with isocyanate and also a non-NCO functional group. This adduct is then reacted with a compound comprising at least one carbamate group or group that can be converted to carbamate and at least one group reactive with the non-NCO functional groups. Examples of non-NCO functional groups include carboxyl, epoxy, hydroxyl, amino. Suitable examples of methods for converting such groups to carbamate or urea groups have already been described above in detail.

Preparation of a compound (b)(2) may also include reaction of one or more of the isocyanate groups with a compound (a) having hydroxyl functionality as described above. Thus, polyisocyanate (b)(2)(B) is reacted with both a compound (b)(2)(A) and a compound (a), either with both concurrently or with each consecutively. At least one isocyanate group, but less than all of the isocyanate groups, is reacted with compound (b)(2)(A), and the remainder of the isocyanate groups is reacted with the compound (a) having the lactone or hydroxy acid moiety.

In yet another preferred embodiment, the second component (b)(2) is a carbamate-functional compound that is the reaction product of a monomeric polyisocyanate(b)(2)(B) and a compound (b)(2)(A) comprising a group that is reactive with isocyanate and a carbamate group or group that can be converted into a carbamate, as described above, with the modification that not all of the available isocyanate groups are reacted with the carbamate-containing compound. The remaining isocyanate groups are reacted with a chain extension agent (b)(2)(C). Suitable chain extension agents include, without limitation, polyols such as 1,6-hexanediol, cyclohexanedimethanol (sold as CHDM by Eastman Chemical Co.), 2-ethyl-1,6-hexanediol, 3-hydroxy-2,2-dimethylpropyl 3-hydroxy-2,2-dimethylpropionate (sold by Eastman Chemical Co. as Esterdiol 204), and 1,4-butanediol, 1,5-pentanediol, and neopentyl glycol. In a particularly preferred embodiment, the monomeric isocyanate is a diisocyanate, especially isophorone or hexamethylene diisocyanate and half of the available isocyanate groups are reacted with a compound comprising a group that is reactive with isocyanate and a carbamate group or group that can be converted into a carbamate group, preferably with hydroxypropyl carbamate, and the remaining isocyanate groups are reacted with a polyol, particularly with 2-ethyl-1,6-hexanediol.

The polyol-extended compound may also be synthesized by a first step of reacting an excess of the monomeric polyisocyanate with the polyol to produce an isocyanate-functional product, and then reacting the isocyanate-functional product with a compound comprising a group that is reactive with isocyanate and a carbamate group or group that can be converted into a carbamate as already described. Similarly, part of the isocyanate groups of the monomeric polyisocyanate can be reacted with a lactone or hydroxy-carboxylic acid to produce an ester-modified isocyanate-functional compound. Preferably, the monomeric polyisocyanate is an isocyanurate of a diisocyanate, more preferably an isocyanurate of isophorone diisocyanate or an isocyanurate of hexamethylene diisocyanate. Also preferred are compounds in which one or more, but less than all, of the isocyanate groups of the polyisocyanate are linked to a group having a lactone or hydroxy acid moiety.

Finally, the second component (b) can be, or include, a compound (b)(3) having at least two carbamate and/or terminal urea groups and at least four urethane or urea linking groups. Preferred compounds (b)(3) may be represented by any of the structures

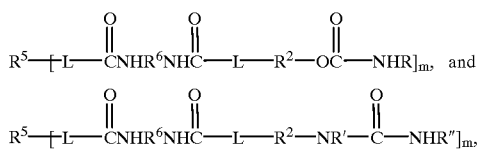

in which R, R', R", $R^2$, L, and m are as previously defined; $R^5$ and $R^6$ are each independently alkylene (including cycloalkylene), preferably having from 1 to about 18 carbon atoms, particularly preferably from about 5 to about 12 carbon atoms, alkylarylene, or arylene, or $R^6$ is a structure that includes a cyanuric ring, a biuret structure, or an allophonate group.

Compound (b)(3) may be prepared by a step of reacting together a compound (b)(3)(A) comprising a carbamate or terminal urea group or a group that can be converted to a carbamate or terminal urea group and also having an isocyanate group and a second compound (b)(3)(B) having at least two groups reactive with isocyanate functionality. The compound (b)(3)(A) preferably has one isocyanate group per molecule. The compound (b)(3)(A) also preferably has a carbamate or terminal urea group, and particularly preferably has a carbamate group. In one embodiment, compound (b)(3)(A) is a reaction product of an hydroxyalkyl carbamate and a polyisocyanate compound. In another embodiments, compound (b)(3)(A) is a reaction product of an hydroxyalkyl cyclic carbonate and a polyisocyanate compound.

The compound (b)(3)(B) having at least two groups reactive with isocyanate functionality may be a diamine or a polyol, preferably a diol. Particularly preferred compounds (b)(3)(B) having at least two groups reactive with isocyanate functionality include linear and branched diols such as 1,6-hexanediol, 2-ethyl-l,6-hexanediol, and neopentyl glycol.

As a third component (c), the coating composition includes a curing agent or crosslinker that is reactive with the first two components, (a) and (b). The curing agent has, on average, at least about two functional groups reactive with the first and second components. The functional groups may be of more than one kind, each kind being reactive with one or both of the first two components.

Useful curing agents include materials having active methylol or methylalkoxy groups, such as aminoplast crosslinking agents or phenol/formaldehyde adducts; curing agents that have isocyanate groups, particularly blocked isocyanate curing agents, curing agents that have epoxide groups, amine groups, acid groups, siloxane groups, cyclic carbonate groups, and anhydride groups; and mixtures thereof. Examples of preferred curing agent compounds include, without limitation, melamine formaldehyde resin (including monomeric or polymeric melamine resin and partially or fully alkylated melamine resin), blocked or unblocked polyisocyanates (e.g., TDI, MDI, isophorone diisocyanate, hexamethylene diisocyanate, and isocyanurates of these, which may be blocked for example with alcohols or oximes), urea resins (e.g., methylol ureas such as urea formaldehyde resin, alkoxy ureas such as butylated urea formaldehyde resin), polyanhydrides (e.g., polysuccinic anhydride), and polysiloxanes (e.g., trimethoxy siloxane). Another suitable crosslinking agent is tris(alkoxy carbonylamino) triazine (available from Cytec Industries under the tradename TACT). The curing agent may be combinations of these, particularly combinations that include aminoplast crosslinking agents. Aminoplast resins such as melamine formaldehyde resins or urea formaldehyde resins are especially preferred. Combinations of tris(alkoxy carbonylamino) triazine with a melamine formaldehyde resin and/or a blocked isocyanate curing agent are likewise suitable and desirable. Component (b) may also contain groups that are reactive with the carbamate group of component (a), such as an acrylic polymer containing polymerized isobutoxymethyl acrylamide groups.

A solvent may optionally be utilized in the coating composition used in the practice of the present invention. Although the composition used according to the present invention may be utilized, for example, in the form of substantially solid powder, or a dispersion, it is often desirable that the composition is in a substantially liquid state, which can be accomplished with the use of a solvent. This solvent should act as a solvent with respect to the components of the composition. In general, the solvent can be any organic solvent and/or water. In one preferred embodiment, the solvent is a polar organic solvent. More preferably, the solvent is selected from polar aliphatic solvents or polar aromatic solvents. Still more preferably, the solvent is a ketone, ester, acetate, aprotic amide, aprotic sulfoxide, aprotic amine, or a combination of any of these. Examples of useful solvents include, without limitation, methyl ethyl ketone, methyl isobutyl ketone, m-amyl acetate, ethylene glycol butyl ether-acetate, propylene glycol monomethyl ether acetate, xylene, N-methylpyrrolidone, blends of aromatic hydrocarbons, and mixtures of these. In another preferred embodiment, the solvent is water or a mixture of water with small amounts of co-solvents.

The coating composition used in the practice of the invention may include a catalyst to enhance the cure reaction. For example, when aminoplast compounds, especially monomeric melamines, are used as a curing agent, a strong acid catalyst may be utilized to enhance the cure reaction. Such catalysts are well-known in the art and include, without limitation, p-toluenesulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine. Other catalysts that may be useful in the composition of the invention include Lewis acids, zinc salts, and tin salts.

In a preferred embodiment of the invention, the solvent is present in the coating composition in an amount of from about 0.01 weight percent to about 99 weight percent, preferably from about 10 weight percent to about 60 weight percent, and more preferably from about 30 weight percent to about 50 weight percent.

Coating compositions can be coated on the article by any of a number of techniques well-known in the art. These include, for example, spray coating, dip coating, roll coating, curtain coating, and the like. For automotive body panels, spray coating is preferred.

Additional agents, for example surfactants, fillers, stabilizers, wetting agents, dispersing agents, adhesion promoters, UV absorbers, hindered amine light stabilizers, etc. may be incorporated into the coating composition. While such additives are well-known in the prior art, the amount used must be controlled to avoid adversely affecting the coating characteristics.

The coating composition according to the invention is preferably utilized in a high-gloss coating and/or as the clearcoat of a composite color-plus-clear coating. High-gloss coatings as used herein are coatings having a 20° gloss (ASTM D523-89) or a DOI (ASTM E430-91) of at least 80.

When the coating composition of the invention is used as a high-gloss pigmented paint coating, the pigment may be any organic or inorganic compounds or colored materials, fillers, metallic or other inorganic flake materials such as mica or aluminum flake, and other materials of kind that the art normally includes in such coatings. Pigments and other insoluble particulate compounds such as fillers are usually used in the composition in an amount of 1% to 100%, based on the total solid weight of binder components (i.e., a pigment-to-binder ratio of 0.1 to 1).

When the coating composition according to the invention is used as the clearcoat of a composite color-plus-clear coating, the pigmented basecoat composition may any of a number of types well-known in the art, and does not require explanation in detail herein. Polymers known in the art to be useful in basecoat compositions include acrylics, vinyls, polyurethanes, polycarbonates, polyesters, alkyds, and polysiloxanes. Preferred polymers include acrylics and polyurethanes. In one preferred embodiment of the invention, the basecoat composition also utilizes a carbamate-functional acrylic polymer. Basecoat polymers may be thermoplastic, but are preferably crosslinkable and comprise one or more type of crosslinkable functional groups. Such groups include, for example, hydroxy, isocyanate, amine, epoxy, acrylate, vinyl, silane, and acetoacetate groups. These groups may be masked or blocked in such a way so that they are unblocked and available for the crosslinking reaction under the desired curing conditions, generally elevated temperatures. Useful crosslinkable functional groups include hydroxy, epoxy, acid, anhydride, silane, and acetoacetate groups. Preferred crosslinkable functional groups include hydroxy functional groups and amino functional groups.

Basecoat polymers may be self-crosslinkable, or may require a separate crosslinking agent that is reactive with the functional groups of the polymer. When the polymer comprises hydroxy functional groups, for example, the crosslinking agent may be an aminoplast resin, isocyanate and blocked isocyanates (including isocyanurates), and acid or anhydride functional crosslinking agents.

The coating compositions described herein are preferably subjected to conditions so as to cure the coating layers. Although various methods of curing may be used, heat-curing is preferred. Generally, heat curing is effected by exposing the coated article to elevated temperatures provided primarily by radiative heat sources. Curing temperatures will vary depending on the particular blocking groups used in the cross-linking agents, however they generally range between 90° C. and 180° C. The first compounds according to the present invention are preferably reactive even at relatively low cure temperatures. Thus, in a preferred embodiment, the cure temperature is preferably between 115° C. and 150° C., and more preferably at temperatures between 115° C. and 140° C. for a blocked acid catalyzed system. For an unblocked acid catalyzed system, the cure temperature is preferably between 80° C. and 100° C. The curing time will vary depending on the particular components used, and physical parameters such as the thickness of the layers, however, typical curing times range from 15 to 60 minutes, and preferably 15–25 minutes for blocked acid catalyzed systems and 10–20 minutes for unblocked acid catalyzed systems.

The invention is further described in the following examples. The examples are merely illustrative and do not in any way limit the scope of the invention as described and claimed. All parts are parts by weight unless otherwise noted.

PREPARATION 1

A suitable reactor equipped with agitator, thermocouple, and nitrogen gas inlet was charged with 477.6 grams of hydroxypropyl carbamate, 1419.5 grams of epsilon-caprolactone, and 2.8 grams of stannous octoate under a blanket of nitrogen. The mixture was heated to 130° C. and that temperature was maintained for 2.5 hours. The reaction product was then cooled and 143 grams of propylene glycol monomethyl ether acetate were added.

PREPARATION 2

A carbamate functional intermediate was prepared as follows. A suitable reactor equipped with agitator, thermocouple, and nitrogen gas inlet was charged with 238.5 grams of hydroxypropyl carbamate, 571.6 grams of epsilon-caprolactone, 1.4 grams of stannous octoate, and 88.6 grams of toluene under a blanket of nitrogen. The mixture was heated to complete the reaction. The carbamate functional intermediate product was then cooled.

The Preparation 2 Resin was prepared using the carbamate functional intermediate product as follows. A suitable reactor equipped with agitator, thermocouple, and nitrogen gas inlet was charged with 294.3 grams of isophorone diisocyanate under a blanket of nitrogen. A total of 1189.7 grams of the carbamate functional intermediate product was added in three portions to the reactor over a period of 1.25 hours. During this time, the temperature of the reaction mixture was allowed to rise to 77° C. The reactor was then heated to 80° C., and this temperature was maintained for 5 hours, at which time all of the isocyanate functionality had been consumed. The reaction product was cooled and 266 grams of propylene glycol monomethyl ether acetate were added.

PREPARATION 3

A total of 163.4 parts by weight of urethane quality amyl acetate was heated under an inert atomosphere to 60° C. and at that temperature 440.83 parts by weight of T-1890 (70% in amyl acetate, available from CreaNova) and an additional 36.45 parts by weight of amyl acetate were added, followed by 0.15 parts by weight of dibutyltin dilaurate and 12.88 parts by weight of amyl acetate. Following these additions, 143.62 parts by weight of hydroxy propyl carbamate were slowly added. The temperature during the addition was kept below 82° C. When the addition of the hydroxy propyl carbamate was complete 17.39 parts by weight of amyl acetate were added. The reaction mixture was kept at about 80° C. for about 4 hours. After the hold, 6.96 parts by weight of n-butanol, 77.0 parts by weight of isobutanol, and 19.0 parts by weight of amyl acetate were added. The final resin had a measured nonvolatile content of 50.9% by weight and a theoretical equivalent weight (based on the carbamate functionality) of 425.

EXAMPLE 1

A clearcoat coating composition was prepared by mixing together 74.4 grams of the Preparation 1 resin, 92.1 grams of the Preparation 3 resin, 101.2 grams of Resimene® 747, 6.5 grams of a UVA solution, 1.3 grams of a hindered amine light stabilizer, 1.8 grams of a solution of a rheology control agent, 6.5 grams of a blocked sulfonic acid catalyst (25% active by weight), 32.8 grams of n-butanol, 54.6 grams of ethylene glycol monobutyl ether acetate, and 5.6 grams of propylene glycol monomethyl ether acetate.

EXAMPLE 2

A clearcoat coating composition was prepared by mixing together 135.3 grams of the Preparation 2 resin, 86.7 grams of the Preparation 3 resin, 37.1 grams of Resimene® 747, 5.5 grams of a UVA solution, 1.1 grams of a hindered amine light stabilizer, 1.5 grams of a solution of a rheology control agent, 5.5 grams of a blocked sulfonic acid catalyst (25% active by weight), 27.6 grams of n-butanol, and 55.3 grams of ethylene glycol monobutyl ether acetate.

COMPARATIVE EXAMPLE A

A clearcoat coating composition was prepared by mixing together 111.6 grams of the Preparation 1 Resin, 116.1 grams of Resimene® 747, 7.0 grams of a UVA solution, 1.4 grams of a hindered amine light stabilizer, 1.9 grams of a solution of a rheology control agent, 7.0 grams of a blocked sulfonic acid catalyst (25% active by weight), 35.0 grams of n-butanol, 58.3 grams of ethylene glycol monobutyl ether acetate, and 8.4 grams of propylene glycol monomethyl ether acetate.

COMPARATIVE EXAMPLE B

A clearcoat coating composition was prepared by mixing together 180.0 grams of the Preparation 2 Resin, 31.5 grams of of Resimene® 747, 5.0 grams of a UVA solution, 1.0 grams of a hindered amine light stabilizer, 1.4 grams of a solution of a rheology control agent, 5.1 grams of a blocked sulfonic acid catalyst (25% active by weight), 25.3 grams of n-butanol, 50.5 grams of ethylene glycol monobutyl ether acetate, and 52.1 grams of n-butyl acetate.

TESTING OF COATING COMPOSITIONS

Primed plastic panels were coated with a black basecoat and then the clearcoat composition wet-on-wet. The coated panels were cured after application of the clearcoat composition by baking at 120° C. for 30 minutes in a gas-fired oven. The cured clear coat films were 1.5–2.0 mils thick.

The coated panels were subjected to outdoor exposure testing in a Jacksonville, Fla. environmental etch testing program. The amount of environmental etch was rated on a scale of 1 to 10D, with 1 being no or little film damage up to 10 being severe film damage and 10A, 10B, 10C, and 10D being increasingly severe film damage.

| Clearcoat Composition | Etch Rating | Exposure Time (weeks) |
|---|---|---|
| Example 1 | 6 | 7 |
| Comparative Ex. A | 10D | 7 |
| Example 2 | 9 | 14 |
| Comparative Ex. B | 10A | 14 |

The invention has been described in detail with reference to preferred embodiments thereof. It should be understood, however, that variations and modifications can be made within the spirit and scope of the invention.

What is claimed is:

1. A curable coating composition, comprising
   (a) a compound having at least one carbamate group or terminal urea group that is prepared by reacting together:
       (1) a compound comprising a carbamate or terminal urea group or a group that can be converted to a carbamate or terminal urea group and a group that is reactive with (a)(2) and
       (2) a lactone or a hydroxy carboxylic acid,
   (b) a component selected from the group consisting of:
       (1) a resin comprising active hydrogen-containing functional groups that are reactive with component (c),
       (2) a compound having at least one carbamate group or terminal urea group that is prepared by reacting together:
           (A) a compound comprising a carbamate or terminal urea group or a group that can be converted to a carbamate or terminal urea group and a group that is reactive with isocyanate functionality and
           (B) a polyisocyanate,
       (3) a compound having at least one carbamate group or terminal urea group that is prepared by reacting together:
           (A) a compound comprising a carbamate or terminal urea group or a group that can be converted to a carbamate or terminal urea group and an isocyanate group and
           (B) a compound having at least two groups reactive with isocyanate functionality, and mixtures thereof; and
   (c) a curing agent that is reactive with compound (a) and component (b), wherein said carbamate group has a structure

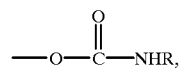

in which R is H or alkyl, and further wherein said terminal urea group has a structure

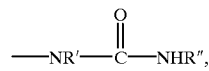

in which R' and R" are each independently H or alkyl, or R' and R" together form a heterocyclic ring structure.

2. A composition according to claim 1, wherein compound (a) has at least one carbamate group.

3. A composition according to claim 1, wherein compound (a)(1) is the isocyanate-functional reaction product of a hydroxyalkyl carbamate and a polyisocyanate.

4. A composition according to claim 3, wherein the hydroxyalkyl carbamate is a β-hydroxyalkyl carbamate and further wherein the polyisocyanate is a diisocyanate or an isocyanurate of a diisocyanate.

5. A composition according to claim 1, wherein the compound (a)(1) has a carbamate or a terminal urea group.

6. A composition according to claim 1, wherein the compound (a)(1) has a carbamate group.

7. A composition according to claim 1, wherein the group on compound (a)(1) that is reactive with compound (a)(2) is a hydroxyl group.

8. A composition according to claim 1, wherein the group on compound (a)(1) that is reactive with compound (a)(2) is an amino group.

9. A composition according to claim 1, wherein compound (a)(1) has one group that is reactive with compound (a)(2).

10. A composition according to claim 7, wherein compound (a)(1) has a carbamate group.

11. A composition according to claim 7, wherein compound (a)(1) has a terminal urea group.

12. A composition according to claim 1, wherein compound (a)(1) is a hydroxyalkyl carbamate.

13. A composition according to claim 8, wherein the hydroxyalkyl carbamate is a β-hydroxyalkyl carbamate.

14. A composition according to claim 1, wherein compound (a)(1) is a hydroxyalkyl cyclic carbonate.

15. A composition according to claim 1, wherein compound (a)(2) is a lactone.

16. A composition according to claim 1, wherein compound (a)(2) is ε-caprolactone.

17. A composition according to claim 15, wherein the ratio of equivalents of lactone to equivalents of the group on compound (a)(1) reactive with the lactone is from about 0.1:1 to about 10:1.

18. A composition according to claim 15, wherein the ratio of equivalents of lactone to equivalents of the group on compound (a)(1) reactive with the lactone is from about 1:1 to about 5:1.

19. A composition according to claim 1, wherein component (b) comprises the resin of (b)(1).

20. A composition according to claim 19, wherein component (b) comprises an acrylic resin, polyurethane resin, polyester resin, or a polyurethane-polyester copolymer resin.

21. A composition according to claim 19, wherein component (b) comprises an acrylic resin.

22. A composition according to claim 19, wherein component (b) comprises a polyester resin or a polyester-polyurethane copolymer resin having a structural moiety resulting from a reaction of a lactone or a hydroxy carboxylic acid.

23. A composition according to claim 19, wherein the resin of component (b) has functionality selected from the group consisting of carbamate functionality, urea functionality, hydroxyl functionality, and combinations thereof.

24. A composition according to claim 19, wherein the resin of component (b) has functionality selected from the group consisting of carbamate functionality, hydroxyl functionality, and combinations thereof.

25. A composition according to claim 19, wherein the resin of component (b) has carbamate functionality.

26. A composition according to claim 1, wherein component (b) comprises a compound (b)(2).

27. A composition according to claim 26, wherein compound (b)(2)(A) is monomeric.

28. A composition according to claim 26, wherein compound (b)(2)(A) has a carbamate group or terminal urea group.

29. A composition according to claim 26, wherein compound (b)(2)(A) has a carbamate group.

30. A composition according to claim 26, wherein compound (b)(2)(A) is a hydroxyalkyl carbamate.

31. A composition according to claim 26, wherein compound (b)(2)(A) is a hydroxyalkyl cyclic carbonate.

32. A composition according to claim 26, wherein the group on compound (b)(2)(A) that is reactive with compound (b)(2)(B) is hydroxyl or amino.

33. A composition according to claim 26, wherein compound (b)(2)(A) has one group that is reactive with compound (b)(2)(B).

34. A composition according to claim 26, wherein compound (b)(2)(B) is an isocyanurate.

35. A composition according to claim 26, wherein compound (b)(2)(B) is selected from the group consisting of hexamethylene diisocyanate, isophorone diisocyanate, isocyanurate of hexamethylene diisocyanate, isocyanurate of isophorone diisocyanate, and mixtures thereof.

36. A composition according to claim 26, wherein preparation of compound (b)(2) includes reacting at least one isocyanate group of polyisocyanate (b)(2)(B) with (b)(2)(C) a compound having at least one carbamate group or terminal urea group that is prepared by reacting together:

(1) a compound comprising a carbamate or terminal urea group or a group that can be converted to a carbamate or terminal urea group and a group that is reactive with (b)(2)(C)(2) and (2) a lactone or a hydroxy carboxylic acid.

37. A composition according to claim 1, wherein component (b) comprises compound (b)(3).

38. A composition according to claim 37, wherein compound (b)(3)(A) has a carbamate or urea group.

39. A composition according to claim 37, wherein compound (b)(3)(A) has a carbamate group.

40. A composition according to claim 37, wherein compound (b)(3)(A) is a reaction product of an hydroxyalkyl carbamate and a polyisocyanate compound.

41. A composition according to claim 37, wherein compound (b)(3)(A) is a reaction product of an hydroxyalkyl cyclic carbonate and a polyisocyanate compound.

42. A composition according to claim 37, wherein compound (b)(3)(B) is a diamine.

43. A composition according to claim 37, wherein compound (b)(3)(B) is a polyol.

44. A composition according to claim 37, wherein compound (b)(3)(B) is a diol.

45. A composition according to claim 1, wherein component (c) is an aminoplast.

46. A composition according to claim 1, wherein component (c) is a melamine formaldehyde resin.

47. A composition according to claim 1, wherein component (c) is a urea formaldehyde resin.

48. A composition according to claim 1, wherein R and R″ are each independently H or alkyl of from 1 to about 4 carbon atoms.

49. A composition according to claim 1, wherein R and R″ are each H.

50. A composition according to claim 1, wherein the composition is a clearcoat coating composition.

51. A composition according to claim 1, further comprising a pigment.

52. An article comprising a substrate having thereon a cured coating derived from a coating composition according to claim 1.

53. An article according to claim 52, wherein said substrate is a flexible substrate.

54. A curable coating composition, comprising (a) a compound selected from the group consisting of compounds having structures

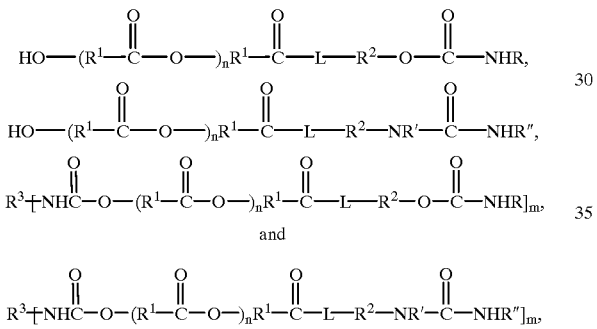

and (b) a component selected from the group consisting of:
(1) a resin comprising active hydrogen-containing functional groups that are reactive with component (c),
(2) a compound selected from the group consisting of compounds having structures

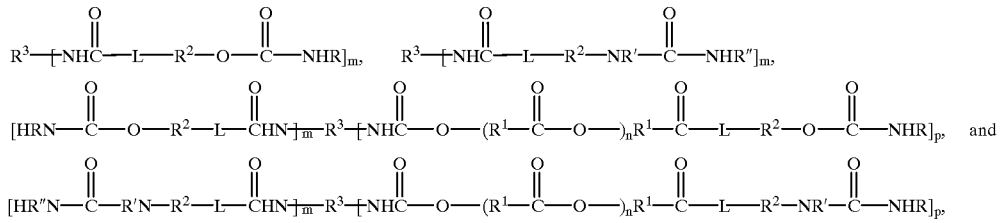

(3) a compound selected from the group consisting of compounds having structures

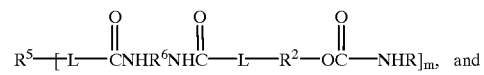

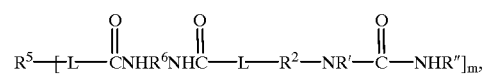

and mixtures thereof; and (c) a curing agent that is reactive with compound (a) and component (b), wherein R is H or alkyl; R' and R″ are each independently H or alkyl, or R' and R″ together form a heterocyclic ring structure; $R^2$ is alkylene or substituted alkylene; $R^1$, $R^3$, $R^5$, and $R^6$ are independently alkylene, cycloalkylene, or arylalkylene, or $R^3$, $R^5$, and $R^6$ are independently arylene, or a structure that includes a cyanuric ring, a urethane group, a urea group, a carbodiimide group, a biuret structure, or an allophonate group; n is from 0 to about 10; m is from 2 to about 6; and L is O, NH, or $NR^4$, where $R^4$ is an alkyl; in which p is from 1 to 5, and m+p is 2 to 6; in which $R^5$ and $R^6$ are each independently alkylene, cycloalkylene, alkylarylene, or arylene, or $R^6$ is a structure that includes a cyanuric ring, a biuret structure, or an allophonate group.

* * * * *